United States Patent
Allum et al.

(10) Patent No.: US 11,918,746 B2
(45) Date of Patent: Mar. 5, 2024

(54) CONCENTRATOR WITH ELECTRONIC HANDHELD REMOTE DELIVERY DEVICE

(71) Applicant: Inogen, Inc., Goleta, CA (US)

(72) Inventors: Todd Allum, Livermore, CA (US); Gregory J. Kapust, San Ramon, CA (US)

(73) Assignee: Inogen, Inc., Goleta, CA (US)

( * ) Notice: Subject to any disclaimer, the term of this patent is extended or adjusted under 35 U.S.C. 154(b) by 0 days.

(21) Appl. No.: 18/154,671

(22) Filed: Jan. 13, 2023

(65) Prior Publication Data

US 2023/0226302 A1 Jul. 20, 2023

Related U.S. Application Data

(63) Continuation of application No. 16/888,502, filed on May 29, 2020, now Pat. No. 11,554,238.

(60) Provisional application No. 62/854,930, filed on May 30, 2019.

(51) Int. Cl.
*A61M 16/10* (2006.01)
*A61M 16/00* (2006.01)

(52) U.S. Cl.
CPC ........ *A61M 16/101* (2014.02); *A61M 16/022* (2017.08); *A61M 2016/1025* (2013.01); *A61M 2202/0208* (2013.01)

(58) Field of Classification Search
CPC .............. A61M 16/101; A61M 16/022; A61M 16/202; A61M 2016/0033; A61M 2202/0208; A61M 2205/3561; A61M 2205/8206; A61M 2016/0027; A61M 2016/1025; A61M 2209/088; A61M 2202/0007

See application file for complete search history.

(56) References Cited

U.S. PATENT DOCUMENTS

| | | | |
|---|---|---|---|
| 8,517,017 B2 * | 8/2013 | Bowditch | A61M 16/06 128/204.23 |
| 8,616,207 B2 * | 12/2013 | Wilkinson | A61M 16/024 96/108 |
| 9,649,464 B2 * | 5/2017 | Wilkinson | A61M 16/0003 |
| 9,833,584 B2 * | 12/2017 | Ahmad | A61M 16/0051 |
| 10,034,991 B2 * | 7/2018 | Homuth | A61M 16/0816 |
| 10,105,509 B2 * | 10/2018 | DeVries | A61M 16/0816 |
| 10,112,025 B2 * | 10/2018 | Bowditch | A61M 16/0066 |
| 10,265,486 B2 * | 4/2019 | Allum | A61M 16/0672 |
| 10,543,327 B2 * | 1/2020 | Jafari | A61M 16/00 |
| 10,556,074 B2 * | 2/2020 | McCarthy | A61M 16/204 |

(Continued)

*Primary Examiner* — Vinh T Lam
(74) *Attorney, Agent, or Firm* — Knobbe, Martens, Olson & Bear, LLP (57) ABSTRACT

A system that enables remote adjustment of oxygen flow from an oxygen source includes a gas source device fluidly coupled to a gas source, a remote delivery device with an outlet for providing gas to a user and an inlet fluidly coupled to an outlet of the gas source device, wherein the gas source device has a control system. The control system determines a current control setting of the remote delivery device based on pneumatic feedback from the remote delivery device and modifies a pressure of gas flowing from the gas source device to the remote delivery device based on the current control setting of the remote delivery device, so that a target flow volume of supply gas associated with the current control setting is delivered to the inlet.

20 Claims, 6 Drawing Sheets

(56) References Cited

U.S. PATENT DOCUMENTS

| | | | |
|---|---|---|---|
| 10,576,237 B2* | 3/2020 | DeVries | A61M 16/101 |
| 10,582,880 B2* | 3/2020 | Sanborn | A61B 5/743 |
| 10,617,839 B2* | 4/2020 | Lucio | C01B 13/02 |
| 10,668,237 B2* | 6/2020 | Schindhelm | A61M 16/0069 |
| 10,729,864 B2* | 8/2020 | Duff | A61M 16/0069 |
| 10,765,822 B2* | 9/2020 | Dong | A61M 16/0051 |
| 10,773,037 B2* | 9/2020 | Adametz | A61M 16/205 |
| 10,821,259 B2* | 11/2020 | Borrello | A61M 16/12 |
| 10,874,809 B2* | 12/2020 | Homuth | A61M 16/00 |
| 10,905,836 B2* | 2/2021 | Ye | A61M 16/0009 |
| 10,905,837 B2* | 2/2021 | Ye | A61M 16/201 |
| 11,090,458 B2* | 8/2021 | Cragg | A61B 5/4809 |
| 11,123,512 B2* | 9/2021 | Allum | B01D 53/0473 |
| 11,129,950 B2* | 9/2021 | Mielcarz | A61M 16/0003 |
| 11,191,914 B2* | 12/2021 | Ahmad | A61M 16/0003 |
| 11,247,009 B2* | 2/2022 | Vicario | A61B 5/7239 |
| 11,253,672 B2* | 2/2022 | Ewers | A61M 16/205 |
| 11,291,785 B2* | 4/2022 | Shahar | A61M 16/204 |
| 11,298,486 B2* | 4/2022 | Grashow | A61M 16/0051 |
| 11,351,334 B2* | 6/2022 | Chalvignac | A61M 16/205 |
| 11,364,359 B2* | 6/2022 | Wilkinson | A61B 5/0816 |
| 11,389,608 B2* | 7/2022 | Borrello | A61M 16/026 |
| 11,433,211 B2* | 9/2022 | Campana | A61B 5/087 |
| 11,452,824 B2* | 9/2022 | Sing | A61M 16/024 |
| 11,458,274 B2* | 10/2022 | Nebrigac | A61M 16/101 |
| 11,497,867 B2* | 11/2022 | Costella | G01N 15/0211 |
| 11,554,238 B2 | 1/2023 | Allum et al. | |
| 11,642,042 B2* | 5/2023 | Milne | A61M 16/024 600/529 |
| 11,666,801 B2* | 6/2023 | Meyer | A61B 5/097 482/13 |
| 11,684,736 B2* | 6/2023 | Liu | A61M 16/022 128/200.24 |
| 11,717,633 B2* | 8/2023 | Peter | A61M 16/0891 128/202.22 |
| 2006/0124128 A1 | 6/2006 | Deane et al. | |
| 2008/0053443 A1* | 3/2008 | Estes | A61M 16/0069 128/204.26 |
| 2013/0275139 A1* | 10/2013 | Coleman | A61M 16/0683 704/E11.001 |
| 2014/0216453 A1* | 8/2014 | Whitcher | A61M 16/10 128/202.26 |
| 2019/0184210 A1* | 6/2019 | Placik | A61M 16/06 |
| 2020/0384238 A1* | 12/2020 | Blunsden | A61M 16/208 |

* cited by examiner

CONCENTRATOR WITH ELECTRONIC HANDHELD REMOTE DELIVERY DEVICE

CROSS-REFERENCE TO RELATED APPLICATIONS

The present application is a continuation of U.S. application Ser. No. 16/888,502, filed May 29, 2020, now U.S. Pat. No. 11,554,238, which claims the priority benefit of U.S. Provisional Application No. 62/854,930, filed May 30, 2019. The subject matter of each of these related applications is hereby incorporated by reference in its entirety.

BACKGROUND

Field of the Various Embodiments

The various embodiments relate generally to medical devices and, more specifically, to a concentrator with an electronic handheld remote delivery device.

Description of the Related Art

Oxygen therapy is the standard of care for many patients with early to mid-stage lung diseases. In particular, individuals with chronic obstructive pulmonary disease (COPD), the third leading cause of death in the United States, are prescribed with oxygen therapy to increase blood oxygen saturation. Individuals that require such oxygen therapy typically have a centralized oxygen source within their home. Oxygen sources can be either liquid oxygen canisters, high-pressure oxygen cylinders, or oxygen concentrators.

Stationary and portable oxygen concentrators utilize a process called pressure swing adsorption (PSA) to increase the oxygen concentration of the incoming ambient air before it is delivered to the patient. Generally, the delivered oxygen concentration is between 90 and 96% due to concentrator efficiencies and remaining constituent elements in the air that does not get adsorbed in the process. Other terminology and/or derivatives of this process have been developed: Rapid Pressure Swing Adsorption (RPSA), Vacuum Pressure Swing Adsorption (VPSA), etc.

Stationary oxygen concentrators use this process to deliver a constant flow of oxygen to the patient, typically 1 to 10 LPM. Some portable oxygen concentrators cannot generate enough oxygen for a therapeutic level of continuous oxygen, rather they provide a small pulse or bolus (~10 ml) upon the detection of an inspiratory effort, which typically is a net delivery of 0.25 TO 1.5 LPM. Spontaneous delivery of oxygen during the inspiratory phase has proven to be sufficient therapy for patients with requirement for supplemental oxygen. Both stationary and portable oxygen concentrators deliver oxygen to the patient through a nasal cannula.

Because state-of-the-art oxygen concentrators produce undesirable levels of noise and heat during operation, oxygen concentrators are typically maintained in a remote location within the home—usually in a different room than that occupied by the user. Similarly, liquid oxygen canisters and high-pressure oxygen cylinders are bulky and heavy, and typically remain in a fixed, out-of-the-way location. Therefore, to enable a user to move freely about the home, long segments of extension tubing (for example >10 foot lengths) are used to connect the user's nasal cannula to the home oxygen source. The use of extension tubing also allows oxygen sources to be placed in locations that are isolated from normal traffic areas in the home.

One drawback to remotely locating an oxygen source within a home or residence is that a user is usually a considerable distance away from the flow controls of the oxygen source, which prevents the user from being able to control the flow of oxygen from the oxygen source from his/her currant location. This problem is exacerbated by the fact that oxygen needs are highly dependent on the user's current activity level, such as sitting, standing, or walking.

For example, a typical user complaint is that they need to turn the source flow to an elevated level to enable the user to walk to a different location within the home, but then, once stationary in the new location (seated or laying down), the user's oxygen needs are reduced and they would prefer to turn the source flow to a lower level as their oxygen requirements are reduced. In addition, the oxygen gas has a low relative humidity and excessive flow rates create nasal drying. Unfortunately, once the user has walked to the new location, he/she is not able to reduce the flow of oxygen without assistance from another person and the act of returning to the oxygen source to change the setting and then walking back to the seated location would require the undesired elevated flow setting. The user is typically forced to set the oxygen flow rate to a level that is not ideal for either sitting or ambulating.

As the foregoing illustrates, what is needed in the art are more effective ways to remotely adjust oxygen levels and therapy when connected to an oxygen source.

SUMMARY

One embodiment of the present disclosure sets forth a technique for remotely adjusting oxygen flow from an oxygen source that is distal to a user. In the embodiment, a system includes a gas source device fluidly coupled to a gas source, a remote delivery device with an outlet for providing gas to a user and an inlet fluidly coupled to an outlet of the gas source device, wherein the gas source device has a control system. The control system determines a current control setting of the remote delivery device based on pneumatic feedback from the remote delivery device and modifies a pressure of gas flowing from the gas source device to the remote delivery device based on the current control setting of the remote delivery device, so that a target flow volume of supply gas associated with the current control setting is delivered to the inlet.

At least one technical advantage of the disclosed techniques relative to the prior art is that the disclosed techniques enable a user to remotely adjust the flow volume of a supply gas, such as oxygen, with a handheld device that is remote from the gas source. Thus, a user can increase a supply gas flow volume from the gas source while ambulating and then, when stationary, can reduce the supply gas flow volume as needed. Another technical advantage of the disclosed techniques is that a flow control system for a supply gas can be configured to deliver multiple types of oxygen therapy, such as the industry standard constant flow oxygen delivery and inspiratory-triggered volume delivery. A further technical advantage of the disclosed techniques is that a flow control system can facilitate oxygen therapy in entrainment ventilation, which typically has higher delivery flow rates and provides positive pressure ventilation. This technical advantage represents one or more technological improvements over prior art approaches.

BRIEF DESCRIPTIONS OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

In the following description, numerous specific details are set forth to provide a more thorough understanding of the embodiments. However, it will be apparent to one of skill in the art that the embodiments may be practiced without one or more of these specific details.

Gas Delivery System

Figure 1:
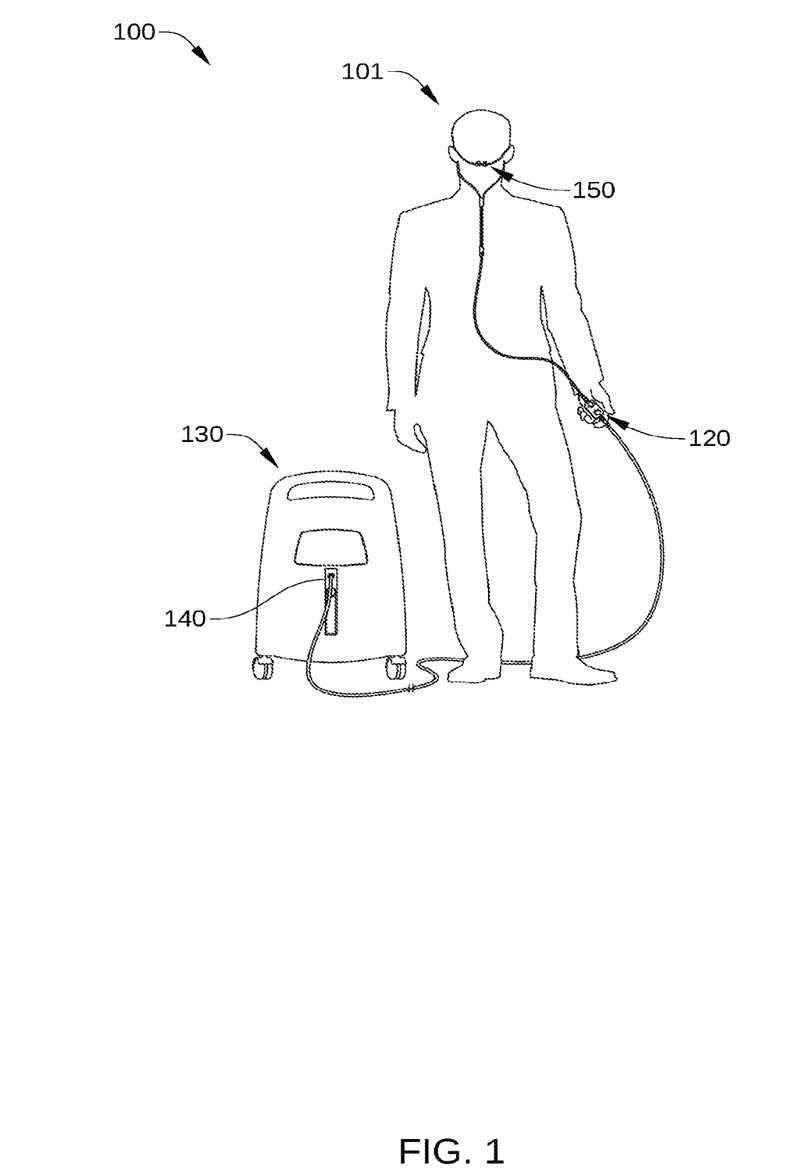
FIG. 1 illustrates an oxygen delivery system configured to implement one or more aspects of the various embodiments.

FIG. 1 illustrates an oxygen delivery system 100 configured to implement one or more aspects of the various embodiments. Oxygen delivery system 100 includes a remote delivery device 120, a gas source 130 with a gas source device 140, and a user interface device 150. As shown, gas source device 140 is pneumatically coupled to gas source 130, and remote delivery device 120 is pneumatically coupled to user interface device 150 and to as source 130 via gas source device 140.

In operation, gas source device 140 determines a current setting of remote delivery device 120 and adjusts the flow volume of supply gas delivered to remote delivery device 120 accordingly. For example, when a user changes a setting at remote delivery device 120, gas source device 140 determines the new setting of remote delivery device 120, determines a current flow volume (rate of flow) to remote delivery device 120, and compares the current flow volume to the target rate flow volume for the new setting of remote delivery device 120. Based on the current flow volume, gas source device 140 increases or decreases the flow volume of supply gas delivered to remote delivery device 120. Such a change in the flow volume of supply gas is determined without feedback from a flow sensor included in remote delivery device 120 or in user interface device 150. Thus, oxygen delivery system 100 is configured to enable remote adjustment to a flow of a supply gas from gas source 130 (for example, oxygen), so that a user 101 can adjust flow volume of the supply gas based on his or her needs at any time. Consequently, user 101 can increase the supply gas flow volume from gas source 130 via remote delivery device 120 while ambulating and then, when stationary, can reduce the supply gas flow volume as needed.

User interface device 150 is pneumatically coupled to remote delivery device 120 and is configured as an interface that facilitates delivery of a supply gas to user 101. As such, user interface device 150 receives supply gas via remote delivery device 120 at a particular flow volume and provides the supply gas to user 101. User interface device 150 can be configured to provide supply gas to user 101 in any technically feasible way. For example, in some embodiments, user interface device 150 includes a nasal cannula nasal pillow for providing supply gas to the nostrils of user 101. Alternatively or additionally, in some embodiments user interface device 150 includes a partial or full-face face mask for providing supply gas to the nostrils and mouth of user 101. Alternatively or additionally, in some embodiments user interface device 150 includes a mouthpiece for providing supply gas to the mouth of user 101.

Gas source 130 can be any technically feasible source of supply gas, such as a tank or an oxygen concentrator. In some embodiments, gas source 130 is configured as a stationary or substantially stationary apparatus, and can be difficult to move about even within a home environment. As a result, in such embodiments, gas source 130 is usually boated remotely from user 101. In embodiments in which gas source 130 is wheeled and somewhat movable, as shown in FIG. 1, there can be significant heat dissipation and noise associated with gas source 130, such as when gas source 130 is configured as an oxygen concentrator. As a result, in such embodiments, gas source 130 is frequently located remotely from user 101, such as in a different room than that occupied by user 101.

Remote delivery device 120 is a portable device configured to control delivery of supply gas to user 101 based on a current setting of remote delivery device 120 that has been selected by user 101. In some embodiments, remote delivery device 120 is implemented as a handheld device. One such embodiment is illustrated in FIG. 2.

Figure 2:
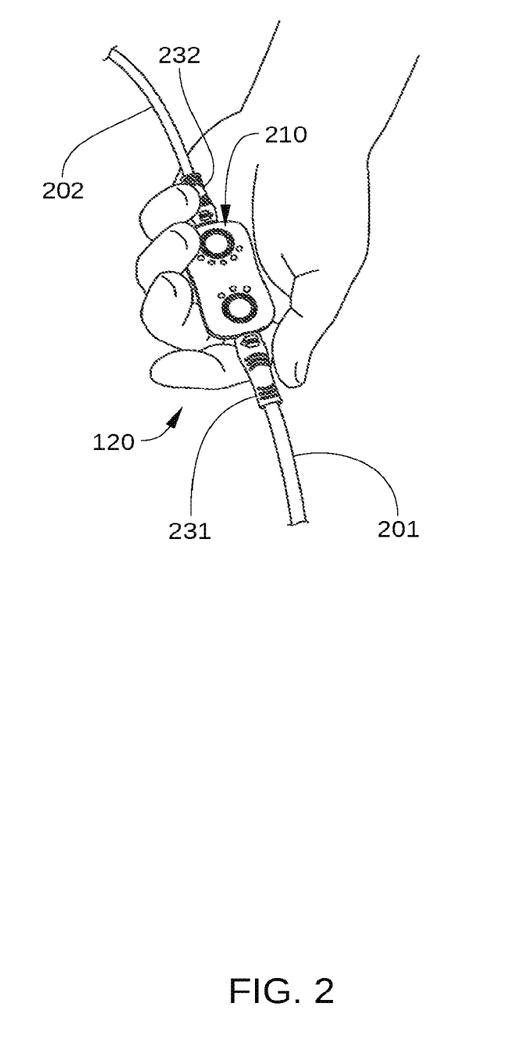
FIG. 2 is a closer view of the remote delivery device of FIG. 1, according to various embodiments.

FIG. 2 is a closer view of remote delivery device 120, according to various embodiments. Remote delivery device 120 includes one or more user input devices 210 that enable user 101 to select a specific setting for the flow volume of supply gas to user 101 and/or a specific therapy mode of remote delivery device 120. Thus, in some embodiments, user 101 selects a desired setting for the flow volume of supply gas via one or more of user input devices 210. Alternatively or additionally, in some embodiments, user 101 selects a desired therapy mode for remote delivery device 120 via one or more of user input devices 210, such as constant flow mode or intermittent flow mode. Input devices 210 can include one or more of a mechanical button, a capacitive button, a switch, a dial, a slider, a touchpad, and the like.

Remote delivery device 120 further includes an inlet 231 and an outlet 232. Inlet 231 is fluidly coupled, for example via flexible gas tubing 201 to gas source device 140 (not shown), and outlet 232 is fluidly coupled, for example via flexible gas tubing 202, to user interface device 150 (not shown). Because gas source device 140 is typically disposed in a remote location from user 101, flexible gas tubing 201 is generally 10 feet or greater in length. In addition, flexible gas tubing 201 is pressurized to a specified level via a regulator or other pressure control device included in gas source device 140.

In the embodiment illustrated in FIG. 2, remote delivery device 120 is configured as a handheld device. In other embodiments, remote delivery device 120 may have a different portable configuration, such as a control pendant configuration, a belt-clip configuration, and the like.

As noted above, when user 101 selects a particular setting via one or more of input devices 210, remote delivery device 120 modifies the flow volume of supply gas in response. Gas source device 140 then determines the current setting of remote delivery device 120 and controls delivery of supply gas to user 101 based on the current setting of remote delivery device 120. In some embodiments, remote delivery device 120 modifies the flow volume of supply gas via a flow control device included in remote delivery device 120. One such embodiment is described below in conjunction with FIG. 3.

Figure 3:
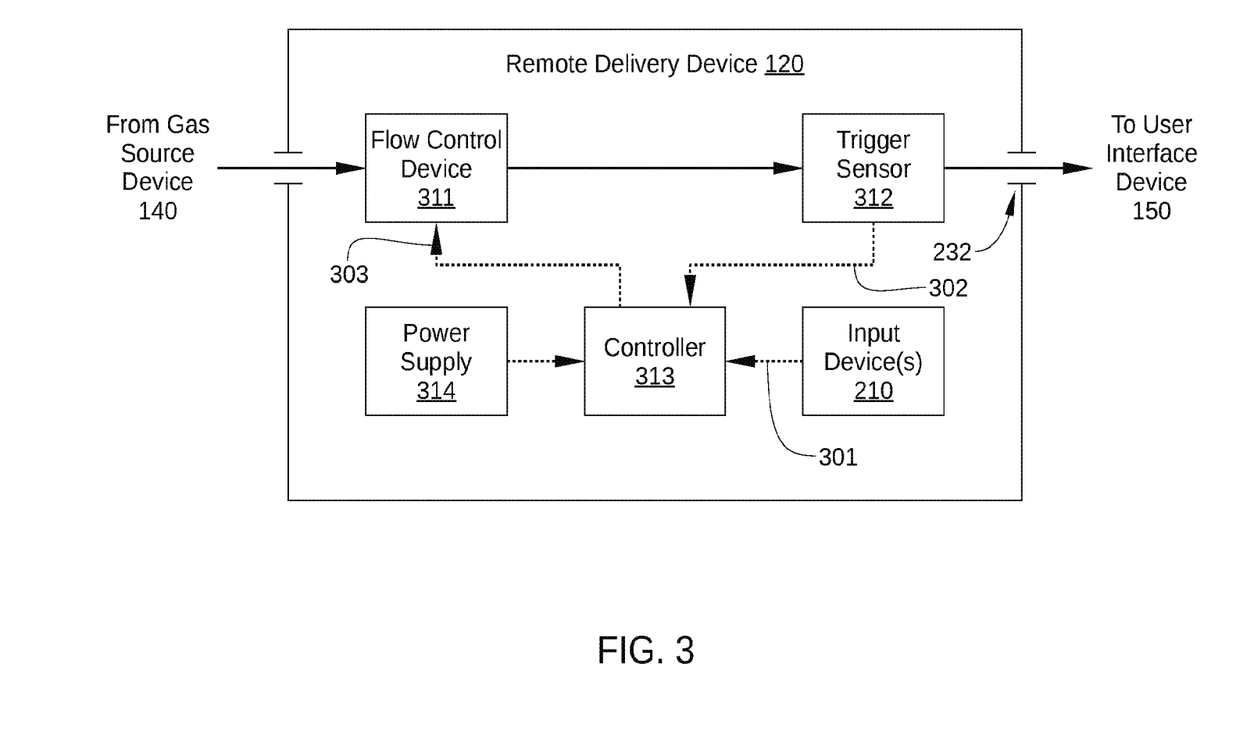
FIG. 3 is a more detailed illustration of the remote delivery device of FIG. 1, according to various embodiments.

FIG. 3 is a more detailed illustration of remote delivery device 120, according to various embodiments. As shown, remote delivery device includes a flow control device 311 (such as a control valve), a trigger sensor 312, a controller 313, a power supply 314 (such as a battery) and one or more input devices 210. Flow control device 311 is configured to control flow volume of supply gas passing through remote delivery device 120 in response to a control signal 303 from controller 313. For example, in some embodiments, flow control device 311 is implemented as a solenoid or proportional valve. Trigger sensor 312 can be a pressure sensor configured to measure a difference between a user pressure, such as that measured at outlet 232, and an ambient pressure, such as that measured external to remote delivery device 120. As such, trigger sensor 312 can detect when a user begins inhaling and a bolus of supply gas is to be provided by remote delivery device 120. Trigger sensor 312 is further configured to generate a trigger signal 302 in response to a trigger threshold being exceeded, such as a measured differential pressure between the user pressure at outlet 232 and the ambient pressure external to remote delivery device 120. Alternatively, trigger sensor 312 is configured to generate a value for trigger signal 302 continuously, where the value indicates a current differential pressure between the user pressure and the ambient pressure. In such embodiments, controller 313 determines whether a trigger threshold is exceeded.

Controller 313 is configured to generate control signal 303 for adjusting flow control device 311 based on input signal 301 from input device(s) 210 and in some embodiments, on trigger signal 302 from trigger sensor 312. Controller 313 can be implemented as any suitable computing device, such as a stand-alone chip (e.g., a microprocessor), an application-specific integrated circuit (ASIC), a system-on-a-chip (SoC), and the like.

In some embodiments, controller 313 is configured to operate in a flow mode. In such embodiments, controller 313 configured to generate a specific control signal 303 for each different setting available to be selected by input device(s) 210. In such embodiments, each setting corresponds to a different target flow volume of supply gas to a user and, thus, a different flow control position of flow control device 311. Thus, in response to a particular input signal 301 from input device(s) 210, controller 313 is configured to generate a corresponding control signal 303 to adjust flow control device 311 appropriately.

Alternatively or additionally, in some embodiments, controller 313 is configured to operate in an intermittent flow mode. In such embodiments, controller 313 is configured to generate a specific control signal 303 for each different setting available to be selected by input device(s) 210, where each setting corresponds to a different target flow volume of supply gas to a user. In such embodiments, each setting may correspond to a different time interval during which flow control device 311 remains open to allow a bolus of supply gas to be supplied to a user. Thus, in response to a particular input signal 301 from input device(s) 210, controller 313 is configured to generate a corresponding control signal 303 to open flow control device 311 for an appropriate time interval. In this way, a bolus of a specified volume of supply gas is provided to the user when inhalation is detected, for example by trigger sensor 312. In alternative embodiment, in response to a particular input signal 301 from input device(s) 210, controller 313 is configured to employ a different combination of time interval and flow control position of flow control device 311 to generate a different flow volume of supply as to a user for each setting available to be selected by input device(s) 210.

In some embodiments, controller 313 is further configured to cause flow control device 311 to perform one or more specific actions in response to a user selecting a new flow volume setting for remote delivery device 120. In such embodiments, gas source device 140 can then determine the flow volume setting selected by the user based on the one or more specific actions performed by flow control device 311. For instance, in some embodiments, when remote delivery device 120 is in a flow mode, controller 313 is configured to cause flow control device 311 to cycle open and closed a specified number of times in a specified time interval in response to a user selecting a new flow volume setting for remote delivery device 120. In such embodiments, the number of times flow control device 311 cycles open and closed in the specified time interval (e.g., one second) indicates a specific setting of remote delivery device 120. In some embodiments, when remote delivery device 120 is in an intermittent flow mode, in response to a user selecting a new flow volume setting for remote delivery device 120, controller 313 is configured to cause flow control device 311 to remain open for a specified time interval and then cycle closed. In such embodiments, the duration of time interval that flow control device 311 remains open indicates a specific setting of remote delivery device 120. In the above embodiments, gas source device 140 can detect specific actions performed by flow control device 311 based on flow rate and/or pressure measurements at an outlet of gas source device 140.

Returning to FIG. 1, gas source device 140 can be mounted to gas source 130, incorporated into gas source 130, or disposed proximate gas source 130. Gas source device 140 is fluidly coupled to an outlet of gas source 130 and is configured to determine the current therapy mode of a user (e.g., flow mode or intermittent flow mode). In addition, gas source device 140 is configured to determine a current flow rate setting of remote delivery device 120, which s typically user-selected. Based on the determined flow rate setting of remote delivery device 120, gas source device 140 controls flow of supply gas from gas source 130 to remote delivery device 120. In this way, a target flow volume of supply gas that corresponds to the current flow rate setting of remote delivery device 120 is delivered to the user through remote delivery device 120. One embodiment of gas source device 140 is described below in conjunction with FIG. 4.

Figure 4:
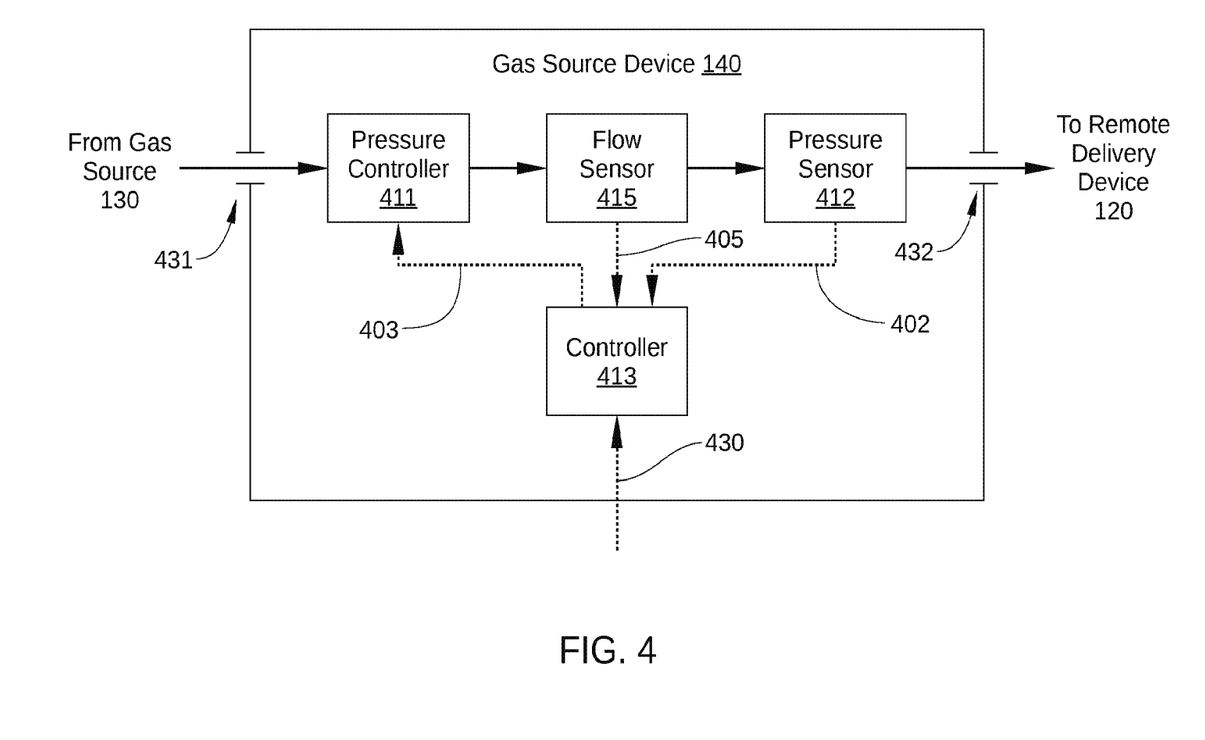
FIG. 4 is a more detailed illustration of the gas source device of FIG. 1, according to various embodiments.

FIG. 4 is a more detailed illustration of gas source device 140, according to venous embodiments. As shown, gas source device 140 includes a pressure controller 411, such as a pressure regulator, a pressure sensor 412, a controller 413 for controlling the operations of gas source device 140, and a flow sensor 415. Pressure controller 411 is pneumatically coupled to gas source 130 via an inlet 431 and is configured to control flow volume of supply gas through gas source device 140 in response to a control signal 403 from controller 413. For example, in some embodiments, pressure controller 411 controls flow volume of supply gas through gas source device 140 by controlling a pressure of supply gas at an outlet 432 of gas source device 140. Pressure sensor 412 is configured to measure the pressure of supply gas at outlet 432 and generate a corresponding pressure signal 402, and flow sensor 415 is configured to measure flow volume of supply gas through gas source device 140 and generate a corresponding flow signal 405.

Controller 413 can be implemented as any suitable, computing device, such as a stand-alone chip (e.g., a microprocessor), an application-specific integrated circuit (ASIC), a system-on-a-chip (SoC), and so forth. Controller 413, in conjunction with one or more of pressure controller 411, pressure sensor 412, and/or flow sensor 415 forms a control system of gas source device 140. Controller 413 is configured to generate control signal 403 for adjusting pressure controller 411 based on pressure signal 402 from pressure sensor 412, on flow signal 405 from flow sensor 415, and/or on one or more signals 430 from gas source device 130 (e.g., a signal indicating a pressure measured in a product tank of gas source device 130). In some embodiments, when a user changes a current setting value of remote delivery device 120 to a new setting value, controller 413 is configured to determine the new setting value, determine a target flow volume of supply gas that corresponds to the new setting value, and compare the current flow volume of supply gas to the target flow volume. Gas source device 140 is further configured to then adjust the flow volume of supply gas being delivered to remote delivery device 120 accordingly.

As noted above, in some embodiments, controller 413 is configured to determine a new setting value of remote delivery device 120 when selected by a user. In some embodiments, controller 413 is configured to determine the new setting value based on pressure signal 402 from pressure sensor 412 flow signal 405 from flow sensor 415, and/or known flow characteristics of flow control device 311 in remote delivery device 120 (shown in FIG. 3). In such embodiments, flow signal 405 indicates a change in flow volume of supply gas that occurs when a user changes a current setting value of remote delivery device 120 to a new setting value. For example, a user preparing to stand and begin ambulating may want to increase an oxygen flow volume to a level known to be adequate for ambulation. In such embodiments, given a current flow volume (as indicated by flow signal 405), a current outlet pressure (as indicated by pressure signal pressure signal 402), and knowledge of the flow characteristics of flow control device 311 at each available setting, controller 413 can determine the new setting value of remote delivery device 120. Alternatively or additionally, in some embodiments, controller 413 is configured to determine the new setting value based on one or more specific actions performed by flow control device, such as cycling open and closed a specific number of times.

As noted above, in some embodiments, controller 413 is configured to determine a target flow volume of supply gas that corresponds to the new setting value for remote delivery device 120. In such embodiments, controller 431 can use a lookup table that indicates a unique target flow volume of supply gas for each available setting for remote delivery device 120.

As noted above, in some embodiments, controller 413 is configured to determine the current flow volume of supply gas to remote delivery device 120. Wen remote delivery device 120 is in intermittent mode, controller 413 determines the current flow volume to remote delivery device 120 during a time interval in which a bolus of gas is delivered to the user by remote delivery device 120. Alternatively, when remote delivery device 120 is in constant flow mode, controller 413 determines the current flow volume to remote delivery device 120 during any suitable time interval (e.g., from a fraction of a second to up to 10 seconds), since the gas from the gas source is continuously delivered to the user by the remote delivery device.

As noted above, in some embodiments, controller 413 is configured to compare the current flow volume of supply gas to the target flow volume and then adjust the flow volume of supply gas being delivered to remote delivery device 120 accordingly. In some embodiments, once a target flow volume of supply gas is determined, controller 413 employs a proportional gain control system to adjust the flow volume of supply gas via a target outlet pressure. For example, in such embodiments, a current outlet pressure (as indicated by pressure signal 402) can be employed to determine a new target outlet pressure setting for pressure controller 411. In one such embodiment, the new target outlet pressure equals the previous target pressure plus the product of a proportional gain constant and the measured flow volume error. In some embodiments, the measured flow volume error is the target flow volume associated with the new setting value for remote delivery device 120 minus the currently measured flow volume. In such an embodiment, the currently measured flow volume typically integrated over a certain time interval. Further, in such an embodiment, the proportional gain constant can be characterized as part of the design process and programmed into controller 413 or determined in a calibration process of gas source device 140.

In some embodiments, controller 413 is configured to determine a current therapy mode selection of remote delivery device 120. In embodiments in which remote delivery device 120 is coupled to a ventilator and gas source 130 is an oxygen concentrator, remote delivery device 120 is typically employed in an intermittent flow mode. When remote delivery device 120 is in intermittent flow mode, the current therapy mode selection of remote delivery device 120 can be determined by controller 413 based on the distinct step reductions in product pressure that occur in a product tank of the oxygen concentrator. For example, the pressure ramp and overall magnitude of the step reduction in pressure that occur when a user makes an inspiratory effort (and a bolus of supply gas from remote delivery device 120 is supplied to the ventilator) can be detected and quantified by controller 413 to determine that remote delivery device 120 is in an intermittent flow mode. In embodiments in which remote delivery device 120 is coupled to a nasal cannula or nasal pillow, remote delivery device 120 is typically employed in a flow mode. When remote delivery device 120 is in flow mode, the current therapy mode selection of remote delivery device 120 can be determined by controller 413 based on a constant flow of gas being provided by remote delivery device 120 to the user.

Constant Flow Mode

Figure 5:
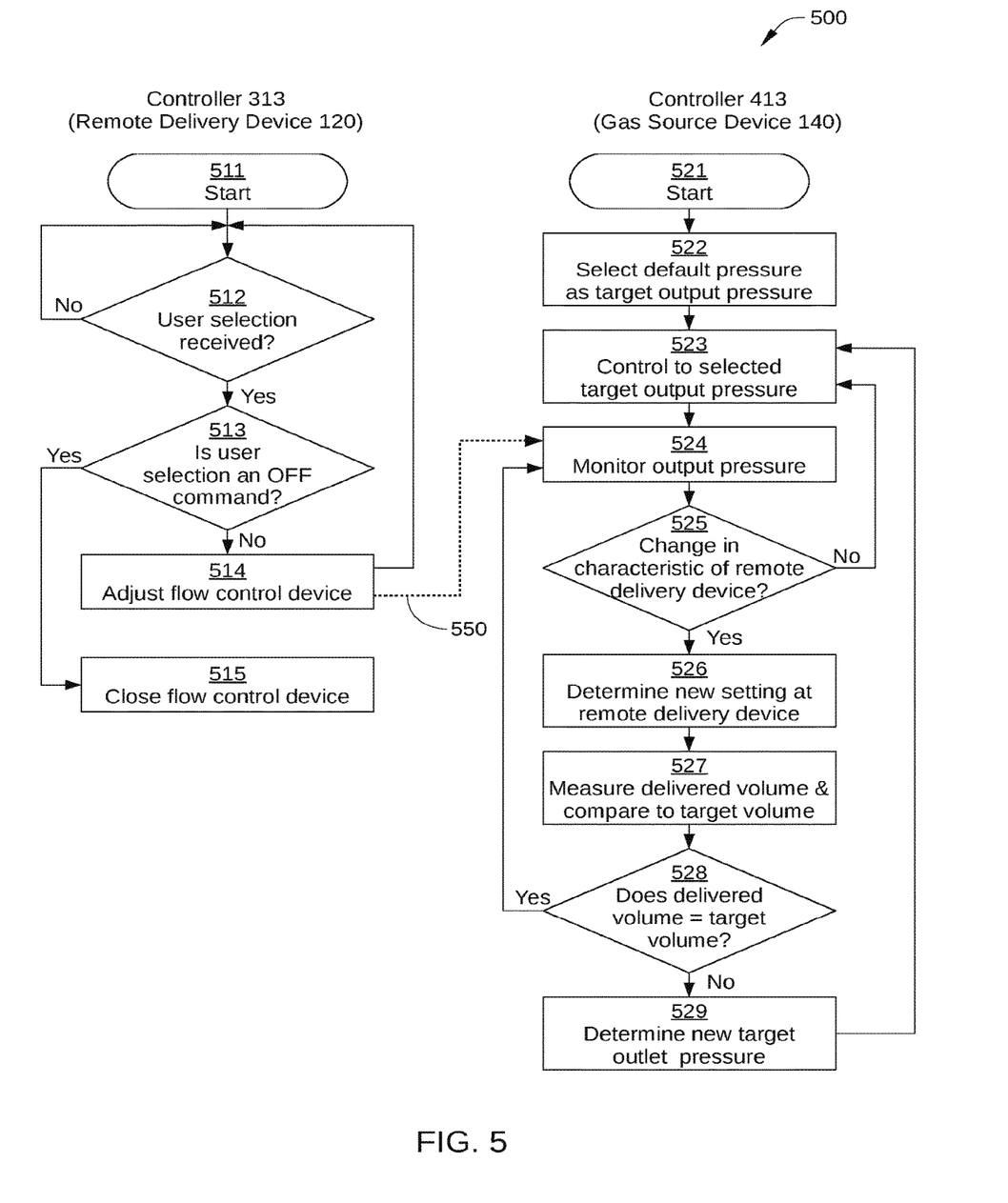
FIG. 5 sets forth a flow diagram of method steps for delivering a supply gas to a user interface device in a constant flow mode, according to various embodiments.

FIG. 5 sets forth a flow diagram of method steps for delivering a supply gas to user interface device 150 in a constant flow mode, according to various embodiments. Although the method steps are described in conjunction with the systems of FIGS. 1-4, persons skilled in the art will understand that any system configured to perform the method steps, in any order, is within the scope of the embodiments. In various embodiments, while in constant flow mode, supply gas is provided continuously to a user at a constant flow volume, where the flow volume is based on a setting value selected by a user on remote delivery device 120. Further, as shown, certain method steps are performed by controller 313 of remote delivery device 120 and certain method steps are performed by controller 413 of gas source device 140. Prior to executing the method steps, remote delivery device 120, gas source 130, and gas source device 140 are pneumatically coupled to each other and turned on.

A method 500 begins at step 511, where controller 313 starts operation of remote delivery device 120. In step 512, controller 313 determines whether a user selection is received, for example via input signal 301 from one or more of input devices 210. If no, method 500 returns step 512; if yes, method 500 proceeds to step 513. In step 513, controller 313 determines whether the received user selection is an OFF command, a zero flow command, or the like. If yes, method 500 proceeds to step 515 and terminates; if no, method 500 proceeds to step 514.

In step 514, controller 313 adjusts flow control device 311 in response to the user selection received in step 512. For example, in some embodiments, controller 313 adjusts flow control device 311 to a specific flow control position that corresponds to the user selection received in step 512. By changing the flow control position of flow control device 311, the pressure-flow characteristic of flow control device 311 changes. As a result, flow through remote delivery device 120 and pressure present at inlet 231 of remote delivery device 120 both change. Such pneumatic feedback 550 is detectable by gas source device 140, for example via flow sensor 415 and/or pressure sensor 412. In some embodiments, in step 514 controller 313 also causes flow control device 311 to perform one or more specific actions, such as cycling open and closed a number of times that indicates the user selection received in step 512. In such embodiments, the one or more specific actions contribute to pneumatic feedback 550, and therefore can be detected by gas source device 140.

In step 515, controller 313 closes flow control device 311 in response to the OFF command received in step 512.

In step 521 controller 413 starts operation of gas source device 140. In step 522, controller 413 selects a default pressure as a target output pressure at outlet 432 of gas source device 140. In step 523, controller 413 controls the output pressure measured at outlet 432 to the target output pressure, for example via pressure controller 411. In step 524, controller 413 monitors the output pressure at outlet 432, which is the pressure in flexible gas tubing 201 between gas source device 140 and remote handheld device 120. Thus, in step 524, controller 413 cart detect pneumatic feedback 550 that occurs in response to flow control device 311. In some embodiments, pneumatic feedback 550 includes a discrete change in flow volume and/or pressure in response to the flow control position of flow control device 311 being changed. In some embodiments, pneumatic feedback 550 further includes a series of changes in flow volume and pressure that occur in response to flow control device 311 performing one or more specific actions, such as cycling open and closed a predetermined number of times.

In step 525, controller 413 determines whether there is a change in the flow characteristic of flow control device 311, for example via pressure sensor 412 and/or flow sensor 415. If no, method 500 returns to step 523 and controller 413 continues to control to the selected target output pressure, if yes, method 500 proceeds to step 526. In step 526, controller 413 determines the new setting at remote delivery device 120, for example based on pressure signal 402 from pressure sensor 412, flow signal 405 from flow sensor 415, and/or known flow characteristics of to control device 311 at the different available settings. In step 527, controller 413 measures the currently delivered flow volume, of supply gas to remote delivery device 120 and compares the measured volume to the target flow volume associated with the new setting at remote delivery device 120.

In step 528, controller 413 determines whether the currently delivered flow volume equals (or is within a threshold value of) the target flow volume associated with the new setting. If yes, method 500 returns to step 524 and controller 413 continues to monitor output pressure of gas source device 140; if no, method proceeds to step 529. In step 529, controller 413 determines a new target outlet pressure. In some embodiments, controller 413 employs a proportional gain control system to determine a new target outlet pressure that adjusts the flow volume of supply gas.

Intermittent Flow Mode

Figure 6:
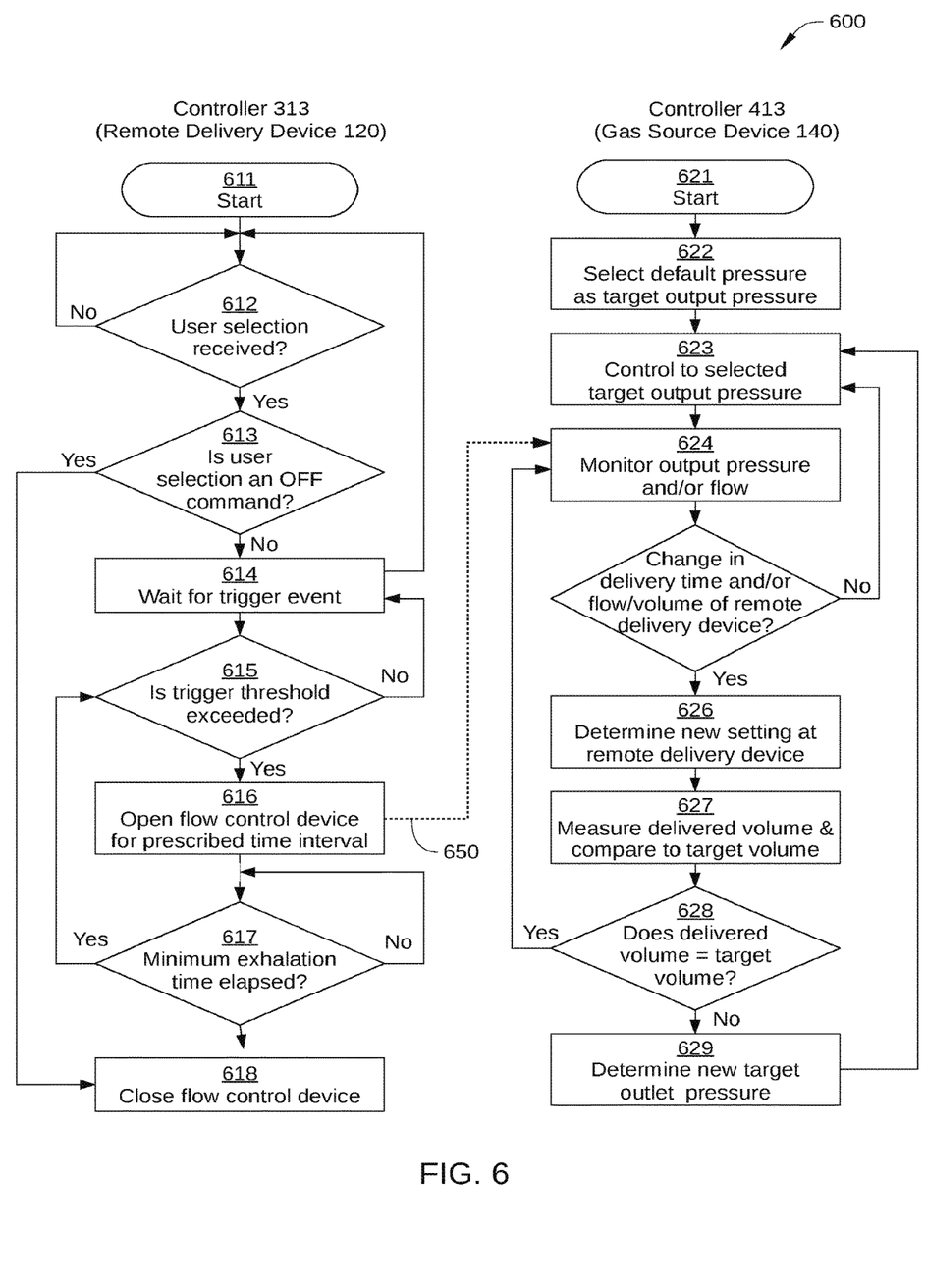
FIG. 6 sets forth a flowchart of method steps for delivering a supply gas to a user interface device in an intermittent flow mode, according to various embodiments.

FIG. 6 sets forth a flowchart of method steps for delivering a supply gas to user interface device 150 in an intermittent flow mode, according to various embodiments. Although the method steps are described in conjunction with the systems of FIGS. 1-4, persons skilled in the art will understand that any system configured to perform the method steps, in any order, is within the scope of the embodiments. In various embodiments, intermittent flow mode, supply gas is provided in a discrete, bolus to a user when inhalation is detected, where the bolus has a specific timing and/or volume. Further, the timing and/or flow volume of the bolus is based on a setting value selected by a user on remote delivery device 120. Thus, for each user-selected setting (e.g., from 1 to 5), remote delivery device 120, operating in conjunction with gas source device 140 and gas source 130, delivers a different volume of gas and or over a time interval of a different duration to the user.

As shown, certain method steps are performed by controller 313 of remote delivery device 120 and certain method steps are performed by controller 413 of gas source device 140. Prior to the method steps, remote delivery device 120, gas source 130, and gas source device 140 are pneumatically coupled to each other and turned on.

A method 600 begins at step 611, where controller 313 starts operation of remote delivery device 120. In step 612, controller 313 determines whether a user selection is received, for example via input signal 301 from one or more of input devices 210. If no, method 600 returns step 612; if yes, method 600 proceeds to step 613. In step 613, controller 313 determines whether the received user selection is an OFF command, a zero flow command, or the like. If yes, method 600 proceeds to step 618 and terminates; if no, method 600 proceeds to step 614.

In step 614, controller 313 waits for detection of a trigger event, for example as indicated by a trigger signal 302 from trigger sensor 312. In step 615, controller 313 determines whether a trigger threshold is exceeded. For example, in some embodiments, controller 313 determines a trigger threshold is exceeded when a value of trigger signal 302 indicates that a differential pressure between the user pressure at outlet 232 and the ambient pressure external to remote delivery device 120 exceeds a threshold value. Generally, such a trigger threshold is exceeded when a user begins inhalation.

In step 616, controller 313 opens flow control device for a prescribed time interval in response to detecting that the trigger threshold is exceeded in step 615. The duration of the prescribed time interval is based on the user selection received in step 612, and/or the patients breath rate. Thus, for higher selection values and delivery of more supply gas, the prescribed time interval is longer in duration and/or the volume delivery is higher, and for lower selection values and delivery of less supply gas, the prescribed time interval is shorter in duration and/or the volume delivery is lower. It is noted that changes in the delivery time and/or volume delivery of remote delivery device 120 can be detected via pneumatic feedback 650 by gas source device 140, for example via flow sensor 415 and/or pressure sensor 415. In step 617, controller 313 determines whether a minimum exhalation time has elapsed since the trigger threshold was exceeded in step 615. If no, method 600 returns to step 617, if yes, method 600 returns to step 615 and controller 313 waits for detection of another trigger event.

In step 618, controller 313 closes flow control device 311 in response to the OFF command received in step 612.

In step 621, controller 413 starts operation of gas source device 140. In step 622, controller 413 selects a default pressure as a target output pressure at outlet 432 of gas source device 140. In step 623, controller 413 controls the output pressure measured at outlet 432 to the target output pressure, for example via pressure controller 411. In step 624, controller 413 monitors the output pressure at outlet 432, which is the pressure in flexible gas tubing 201 between gas source device 140 and remote handheld device 120. Thus, in step 624, controller 413 can detect pneumatic feedback 650 that occurs in response to flow control device 311. In some embodiments, pneumatic feedback 650 includes a discrete change in flow volume and/or pressure in response to the flow control position of flow control device 311 being changed.

In step 625, controller 413 determines whether there is a change in the delivery time and/or volume of flow control device 311, for example via pressure sensor 412 and/or flow sensor 415. If no method 600 returns to step 623 and controller 413 continues to control to the selected target output pressure, if yes, method 600 proceeds to step 626. In some embodiments, a drop in pressure measured by pressure sensor 412 for a period of time followed by a subsequent increase in pressure indicates the time interval during which remote delivery device 120 allows gas to flow to the user, which is the delivery time of flow control device 311. In some embodiments, the rate of drop in pressure measured by pressure sensor 412 indicates the flow rate during which remote delivery device 120 allows gas to flow to the user, which is the delivered flow rate of flow control device 311. Alternatively, in some embodiments, an increase in flow from 0 to some significant flow rate and then returning to 0 indicates the time interval during which remote delivery device 120 allows gas to flow to the user. In some embodiments, the measured flow rate indicates the flow delivered to by remote delivery device 120.

In step 626, controller 413 determines the new setting at remote delivery device 120, for example based on the new delivery time determined in step 625. In step 627, controller 413 measures the currently delivered flow volume of supply gas to remote delivery device 120 and compares the measured volume to the target flow volume associated with the new setting at remote delivery device 120.

In step 628, controller 413 determines whether the currently delivered flow volume equals (or is within a threshold value of) the target flow volume associated with the new setting. If yes, method 600 returns to step 624 and controller 413 continues to monitor output pressure of gas source device 140; if no, method proceeds to step 629. In step 629, controller 413 determines a new target outlet pressure. In some embodiments, controller 413 employs a proportional gain control system to determine a new target outlet pressure that adjusts the flow volume of supply gas.

In sum, the embodiments provide techniques for remotely controlling gas delivery from a gas source, such as a tank or oxygen concentrator. The system includes a gas source device, which is disposed proximate the gas source, and a remote delivery device, which can be carried or held by the user. The gas source device is configured to determine the current therapy mode of a user (e.g., constant flow or intermittent flow). The gas source device is further configured to determine a current flow rate setting of the remote delivery device. Based on the current flow rate setting of the remote delivery device, the gas source device controls flow of supply gas from the gas source to the remote delivery device so that a target flow volume of supply gas associated with the current flow rate setting is delivered to the patient through the remote delivery device.

At least one technical advantage of the disclosed techniques relative to the prior art is that the disclosed techniques enable a user to remotely adjust the flow volume of a supply gas, such as oxygen, with a handheld device that is remote from the gas source. Thus, a user can increase a supply gas flow volume from the gas source while ambulating and then, when stationary, can reduce the supply gas flow volume needed. Another technical advantage of the disclosed techniques is that a flow control system for a supply gas can be configured to deliver multiple types of oxygen therapy, such as the industry standard constant flow oxygen delivery and inspiratory-triggered volume delivery. A further technical advantage of the disclosed techniques is that a flow control system can facilitate oxygen therapy in entrainment ventilation, which typically has higher delivery flow rates and provides positive pressure ventilation. This technical advantage represents one or more technological improvements over prior art approaches.

1. In some embodiments, a system includes a gas source device fluidly coupled to a gas source; an remote delivery device with an outlet for providing gas to a user and an inlet fluidly coupled to an outlet of the gas source device; wherein the gas source device has a control system that: determines a current control setting of the remote delivery device based on pneumatic feedback from the remote delivery device; and modifies a pressure of gas flowing from the gas source device to the remote delivery device based on the current control setting of the remote delivery device, so that a target flow volume of supply gas associated with the current control setting is delivered to the inlet.

2. The system of cause 1, wherein the control system further determines a current therapy mode of the remote delivery device while the remote delivery device is providing the gas to the outlet for providing gas to the user.

3. The system of clauses 1 or 2, wherein the control system further determines current therapy mode of the remote delivery device based on at least one of a flow of gas measured by a flow sensor included in the gas source device or a pressure change measured by a pressure sensor included in the gas source device.

4. The system of any of clauses 1-3, wherein the control system further determines that the remote delivery device is in an intermittent flow mode based on at least one of a timing of pressure changes measured by a pressure sensor included in the gas source device or a reduction in pressure in a product tank of the gas source.

5. The system of any of clauses 5, wherein the control system further determines that the remote delivery device is in a constant flow mode based on at least one of a lack of pressure changes in the pressure of gas flowing from the gas source device to the remote delivery device during a predetermined time interval or a constant flow volume of gas from the gas source device to the remote delivery device during the predetermined time interval.

6. The system of any of clauses 1-5, wherein the control system further measures the pressure of gas during the predetermined time interval via a pressure sensor included in the gas source device.

7. The system of any of clauses 1-6, wherein the control system further measures the flow volume of gas from the gas source device to the remote delivery device during the predetermined time interval via a flow sensor included in the gas source device.

8. The system of any of clauses 1-7, wherein the control system further determines the current control setting of the remote delivery device based on detection of a specific action performed by the remote delivery device while the remote delivery device provides the gas to the outlet for providing gas to the user.

9. The system of any of clauses 1-8, wherein the specific action comprises cycling a flow control device included in the remote delivery device a predetermined number of times within a specified time interval.

10. The system of any of clauses 1-9, wherein the pneumatic feedback from the remote delivery device comprises at least one of a change in flow volume of gas flowing from the gas source device to the remote delivery device or a change in pressure of gas flowing from the gas source device to the remote delivery device.

11. The system of any of clauses 1-10, wherein the control system measures the change in the flow volume of gas flowing from the gas source device to the remote delivery device via a flow sensor included in the gas source device.

12. The system of any of clauses 1-11, wherein the control system measures the change in pressure of gas flowing from the gas source device to the remote delivery device via a pressure sensor included in the gas source device.

13. In some embodiments, a method includes: at a gas source device that is fluidly coupled to a gas source and a remote delivery device, determining a change a flow characteristic of the remote delivery device based on pneumatic feedback from the remote delivery device; based on the change in the flow characteristic, determining a current control setting of the remote delivery device; and modifying a pressure of gas flowing from the gas source device to the remote delivery device based on the current control setting of the remote delivery device, so that a target flow volume of supply gas associated with the current control setting is delivered to an inlet fluidly coupled to an outlet of the gas source device.

14. The method of clause 13, further comprising, prior to determining the change in the flow characteristic, monitoring a pressure of gas flowing from the gas source device to the remote delivery device.

15. The method of clauses 13 or 14, wherein a pressure sensor included in the gas source device monitors the pressure of gas flowing from the gas source device to the remote delivery device.

16. The method of any of clauses 13-15, wherein the pneumatic feedback from the remote delivery device comprise sat least one of a change in flow volume of gas flowing from the gas source device to the remote delivery device or a change in pressure of gas flowing from the gas source device to the remote delivery device.

17. In some embodiments, a method includes: at a gas source device that is fluidly coupled to a gas source and a remote delivery device, determining a change in a delivery time of the remote delivery device based on pneumatic feedback from the remote delivery device; based on the change in the delivery time, determining a current control setting of the remote delivery device; and modifying a pressure of gas flowing from the gas source device to the remote delivery device based on the current control setting of the remote delivery device, so that a target flow volume of supply gas associated with the current flow rate setting is delivered to an inlet coupled to an outlet of the gas source device.

18. The method of clause 17, wherein the pneumatic feedback from the remote delivery device comprises at least one of a change in flow volume of gas flowing from the gas source device to the remote delivery device or a change in pressure of gas flowing from the gas source device to the remote delivery device.

19. The method of clauses 17 or 13, wherein a flow sensor included in the gas source device measures the change in the flow volume of gas flowing from the gas source device to the remote delivery device.

20. The method of any of clauses 17-19, wherein a pressure sensor included in the gas source device measures the change in pressure of gas flowing from the gas source device to the remote delivery device.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embedment (including firmware, resident software, microcode, etc.) or an embodiment combining software and hardware aspects that may all generally be referred to herein as a "module" a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable medium (s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each blocs of the flowchart illustrations and for block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may some be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A system for providing therapy gases to a subject, the system comprising:
    a gas source device comprising:
        an inlet configured to receive gas from a gas source;
        an outlet;
        a pressure sensor configured to generate one or more signals responsive to detecting pressure of gas at said outlet;
        a flow sensor configured to generate one or more signals responsive to detecting flow volume of gas passing through said gas source device;
        a gas source device controller configured to receive said one or more signals generated by each of said pressure sensor and said flow sensor; and
        a pressure regulator; and
    a first flexible tube comprising a first end and a second end opposite said first end, said first end configured to be connected to said outlet of said gas source device;
    a user interface device for providing said gas to nostrils of a subject;
    a second flexible tube having a first end and a second end opposite said first end of the second flexible tube, said first end of the second flexible tube configured to be connected to said user interface device; and
    a handheld remote delivery device comprising:
        an inlet configured to be connected to said second end of said first flexible tube to facilitate fluid communication with said outlet of said gas source device;
        an outlet configured to be connected to said second end of said second flexible tube to facilitate fluid communication with said user interface device;
        a flow control device comprising at least one valve for controlling gas flow through the handheld remote delivery device;
        a battery;
        one or more user input devices configured to receive an instruction to change the handheld remote delivery device from a first flow setting to a second flow setting; and
        a remote delivery device controller, wherein, in response to receiving said instruction from said one or more user input devices, said remote delivery device controller is configured to:
            cause said at least one valve of said flow control device to cycle between a first position and a second position a plurality of times during a first time interval, said at least one valve being open when in said first position and closed when in said second position; and
            cause said at least one valve of said flow control device to move from a third position associated with said first flow setting to a fourth position associated with said second flow setting, said at least one valve being open when in said fourth position;
    wherein the gas source device controller is configured to:
        determine said change in the handheld remote delivery device from said first flow setting to said second flow setting based on said one or more signals received from said pressure sensor, said one or more signals received from said flow sensor, and said plurality of times said at least one valve of said flow control device cycles between said first and second positions during said first time interval; and
        alter, using said pressure regulator, pressure of gas flowing through said outlet of said gas source device through said first flexible tube and to said handheld remote delivery device based on said determined change in the remote delivery device from said first flow setting to said second flow setting.

2. The system of claim 1, wherein said user interface device comprises one or more nasal pillows.

3. The system of claim 1, wherein said one or more user input devices are further configured to change a current operational mode of the handheld remote delivery device between a constant flow mode and an intermittent flow mode.

4. The system of claim 1, wherein said one or more user input devices comprises one or more mechanical or capacitive buttons.

5. A system for providing therapy gases to a subject, the system comprising:
- a gas source device comprising:
  - an inlet configured to receive gas from a gas source;
  - an outlet;
  - a pressure sensor configured to generate one or more signals responsive to detecting pressure of gas at said outlet;
  - a flow sensor configured to generate one or more signals responsive to detecting flow volume of gas passing through said gas source device;
  - a gas source device controller configured to receive said one or more signals generated by each of said pressure sensor and said flow sensor; and
  - a pressure regulator; and
- a first tube comprising a first end and a second end opposite said first end, said first end configured to be connected to said outlet of said gas source device;
- a user interface device for providing said gas to a subject;
- a second tube having a first end and a second end opposite said first end of the second tube, said first end of the second tube configured to be connected to said user interface device; and
- a handheld remote delivery device comprising:
  - an inlet configured to be connected to said second end of said first tube to facilitate fluid communication with said outlet of said gas source device;
  - an outlet configured to be connected to said second end of said second tube to facilitate fluid communication with said user interface device;
  - a flow control device comprising at least one valve for controlling gas flow through the handheld remote delivery device;
  - a power supply;
  - one or more user input devices configured to receive an instruction to change the handheld remote delivery device from a first flow setting to a second flow setting;
  - a remote delivery device controller, wherein, in response to receiving said instruction from said one or more user input devices, said remote delivery device controller is configured to:
    - cause said at least one valve of said flow control device to move from a first position associated with said first flow setting to a second position associated with said second flow setting; and
  - wherein the gas source device controller is configured to:
    - determine said change in the handheld remote delivery device from said first flow setting to said second flow setting based on said one or more signals received from said pressure sensor and said one or more signals received from said flow sensor; and
    - alter, using said pressure regulator, pressure of gas flowing through said outlet of said gas source device through said first tube and to said handheld remote delivery device based on said determined change in the remote delivery device from said first flow setting to said second flow setting.

6. The system of claim 5, wherein said user interface device comprises one or more nasal pillows configured to secure within nostrils of the subject.

7. The system of claim 5, wherein said one or more user input devices comprises one or more mechanical or capacitive buttons.

8. The system of claim 5, wherein said one or more user input devices are further configured to change a current operational mode of the handheld remote delivery device between a constant flow mode and an intermittent flow mode.

9. The system of claim 8, wherein said handheld remote delivery device further comprises a trigger sensor for detecting inhalation of said subject when said handheld remote delivery device is in said intermittent flow mode, said trigger sensor configured to generate at least one trigger signal in response to a determination that a difference between an outlet pressure at said outlet of said handheld remote delivery device and an ambient pressure exceeds a trigger threshold.

10. The system of claim 9, wherein said trigger sensor is configured to determine that said difference between said outlet pressure at said outlet of said handheld remote delivery device and said ambient pressure exceeds said trigger threshold.

11. The system of claim 9, wherein said remote delivery device controller is configured to:
- receive said at least one trigger signal generated by said trigger sensor; and
- determine that said difference between said outlet pressure at said outlet of said handheld remote delivery device and said ambient pressure exceeds said trigger threshold.

12. The system of claim 5, wherein said at least one valve is open when in both of said first and second positions.

13. The system of claim 5, wherein:
- in response to receiving said instruction from said one or more user input devices, said remote delivery device controller is configured to cause said at least one valve of said flow control device to cycle between a third position and a fourth position a plurality of times during a first time interval, said at least one valve being open when in said third position and closed when in said fourth position; and
- the gas source device controller is further configured to determine said change in the handheld remote delivery device from said first flow setting to said second flow setting based on said one or more signals received from said pressure sensor, said one or more signals received from said flow sensor, and said plurality of times said at least one valve of said flow control device cycles between said third and fourth positions during said first time interval.

14. The system of claim 5, wherein said gas source comprises oxygen.

15. A system for providing therapy gases to a subject, the system comprising:
- a gas source device comprising:
  - an inlet configured to receive gas from a gas source;
  - an outlet;
  - a pressure sensor configured to generate one or more signals responsive to detecting pressure of gas at said outlet;
  - a flow sensor configured to generate one or more signals responsive to detecting flow volume of gas passing through said gas source device; and
  - a gas source device controller configured to receive said one or more signals generated by each of said pressure sensor and said flow sensor; and
- a remote delivery device comprising:
  - an inlet configured to be connected to said outlet of said gas source device via a first tube;

an outlet configured to be connected to a user interface device via a second tube, said user interface device configured to provide said gas to a subject; and a flow control device for controlling gas flow through the remote delivery device;

one or more user input devices configured to receive an instruction to change the remote delivery device from a first flow setting to a second flow setting;

a remote delivery device controller configured to control operation of said flow control device based on said instruction to change said remote delivery device from said first flow setting to said second flow setting;

wherein the gas source device controller is configured to:

determine said change in the remote delivery device from said first flow setting to said second flow setting based on at least one of said one or more signals received from said pressure sensor and said one or more signals received from said flow sensor; and alter at least one of pressure and flow volume of gas flowing through said outlet of said gas source device to said remote delivery device based on said determined change in the remote delivery device from said first flow setting to said second flow setting.

16. The system of claim 15, wherein:

said one or more user input devices are further configured to change a current operational mode of the remote delivery device between a constant flow mode and an intermittent flow mode;

when said remote delivery device is in said constant flow mode, said remote delivery device controller is configured to cause at least one valve of said flow control device to move from a first position associated with said first flow setting to a second position associated with said second flow setting, wherein said at least one valve is open in at least one of said first position and said second position.

17. The system of claim 16, wherein:

said remote delivery device further comprises a trigger sensor for detecting inhalation of said subject when said remote delivery device is in said intermittent flow mode, said trigger sensor configured to generate at least one trigger signal in response to a determination that a difference between an outlet pressure at said outlet of said remote delivery device and an ambient pressure exceeds a trigger threshold.

18. The system of claim 17, wherein said remote delivery device controller is configured to:

receive said at least one trigger signal generated by said trigger sensor; and determine that said difference between said outlet pressure at said outlet of said handheld remote delivery device and said ambient pressure exceeds said trigger threshold.

19. The system of claim 17, wherein:

when said remote delivery device is in said first flow setting and said remote delivery device is in said intermittent flow mode, said remote delivery device is configured to cause said at least one valve to be open for a first time interval in response to said difference exceeding said trigger threshold; and when said remote delivery device is in said second flow setting and said remote delivery device is in said intermittent flow mode, said remote delivery device is configured to cause said at least one valve to be open for a second time interval in response to said difference exceeding said trigger threshold;

said second time interval is different than said first time interval.

20. The system of claim 15, further comprising said user interface device, said first tube, and said second tube, wherein said user interface device comprises two nasal pillows, each nasal pillow configured to secure within a nostril of the subject.

\* \* \* \* \*